United States Patent
Dean et al.

(10) Patent No.: US 7,046,012 B2
(45) Date of Patent: May 16, 2006

(54) IONIZATION DEVICES

(75) Inventors: William Francis Houlton Dean, Cambridge (GB); Mark Julian Stockdale, Harston (GB)

(73) Assignee: Ion Science Limited, Cambridgeshire (GB)

( * ) Notice: Subject to any disclaimer, the term of this patent is extended or adjusted under 35 U.S.C. 154(b) by 25 days.

(21) Appl. No.: 10/479,759

(22) PCT Filed: Nov. 20, 2002

(86) PCT No.: PCT/GB02/05236

§ 371 (c)(1),
(2), (4) Date: Dec. 4, 2003

(87) PCT Pub. No.: WO03/046535

PCT Pub. Date: Jun. 5, 2003

(65) Prior Publication Data

US 2004/0168913 A1    Sep. 2, 2004

(30) Foreign Application Priority Data

Nov. 20, 2001  (GB)  .................................... 0127705
Mar. 22, 2002  (GB)  .................................... 0206769

(51) Int. Cl.
*G01N 27/62* (2006.01)
(52) U.S. Cl. ...................... 324/459; 324/464
(58) Field of Classification Search ........ 324/459–465; 204/424, 431; 73/1.06, 23.2; 205/779.5; 250/423 R, 423 F, 281, 306, 288, 389
See application file for complete search history.

(56) References Cited

U.S. PATENT DOCUMENTS

| | | | | |
|---|---|---|---|---|
| 4,506,226 A | * | 3/1985 | Luce et al. | 324/459 |
| 5,116,764 A | * | 5/1992 | Annino et al. | 436/161 |
| 5,394,090 A | * | 2/1995 | Wentworth et al. | 324/464 |
| 5,644,220 A | * | 7/1997 | Urs et al. | 324/71.3 |
| 5,773,833 A | * | 6/1998 | Hsi | 250/382 |
| 6,320,388 B1 | * | 11/2001 | Sun et al. | 324/464 |
| 6,404,205 B1 | * | 6/2002 | Kitamura | 324/464 |
| 6,524,740 B1 | * | 2/2003 | Broy et al. | 429/61 |

FOREIGN PATENT DOCUMENTS

DE    28 36 671 A1  *  4/1979

* cited by examiner

*Primary Examiner*—Vincent Q. Nguyen
(74) *Attorney, Agent, or Firm*—Jon A. Gibbons; Fleit, Kain, Gibbons, Gutman, Bongini & Bianco P.L.

(57) ABSTRACT

An ionization detector includes a third (fence) electrode (55) between the counter electrode (53) and the sensing electrode (54). The fence electrode (53) is maintained at or near the potential of the sensing electrode (54) and traps charge movement (electrolytic current) along the detector walls associated with condensation and/or contamination within the detector. In a photoionisation detector, the fence electrode is also adapted to trap photo-induced current originating from the cathode (53).

Current drawn from the fence electrode (53) provides a measure of the degree of contamination or condensation within the detector and of lamp efficiency.

24 Claims, 3 Drawing Sheets

IONIZATION DEVICES

CROSS-REFERENCE TO RELATED APPLICATIONS

This application is based upon and claims priority from PCT/GBO2/05236, filed on Nov. 20, 2002, which is based on and claims priority from British Application 0206769.2 filed on Mar. 22, 2002, and claims priority from British Application 0127705.2 filed on Nov. 20, 2001, the entire disclosure of each of the aforementioned applications are each herein incorporated by reference in their entirety.

FIELD OF THE INVENTION

This present invention generally relates to with gas or vapour detectors and methods of operating them, and more particularly relates to devices that involve the detection of ions passing through or across a high-impedance medium (such as air or a ceramic surface). It is especially concerned with such devices that are intended for sampling gases, such as air, for specific additional gaseous constituents.

BACKGROUND OF THE INVENTION

It is frequently desirable to ascertain whether the air in or around a locality such as a factory or a laboratory contains gaseous material that might be harmful or dangerous to health, that might present a fire risk, or that might indicate the failure of equipment designed to contain the material in gaseous or liquid form, and much instrumentation exists to detect and measure such materials (which are known, in the art, as "gaseous analytes"; typical such analytes are petroleum chemicals—propane, butane, hexane and so on, and chlorinated and/or fluorinated hydrocarbons such as methylene chloride).

A typical gas sampling device usually incorporates a pump or fan to draw the gas to be sampled through a probe into the body of the device and there present it to, or through, a suitable gas sensor. Alternatively the gas to be sampled may be presented to, or through, a suitable gas sensor by diffusion without the assistance of a pump or fan.

One particular form of sensor utilises ion detection; the sampled gas is subjected to a physical treatment, such as photoionisation or flame ionisation, that causes any analytes therein to be ionised, and the formed ions are then drawn to an electrode so causing a minute electrical current to flow through the associated detector circuitry. Dependent on their application such sensors fall broadly into one or other of two different types: portable/roaming or fixed.

The portable or roaming gas monitor or detector is, as its name suggests, carried around a site testing for gas. It is particularly useful in tracing leaks of gaseous analytes from their containment means, and in roaming over large areas of an industrial site to ensure a particular analyte is not present in quantities liable to present some risk. Unfortunately, because the temperature of sampled gas varies as the detector is conveyed from place to place, the gas drawn into the monitor may on occasion experience a sufficient drop in temperature to cause dew or mist to form in the sampled gas drawn into the probe. This mist may then condense on the probe walls, and even on or within the gas sensor itself, resulting in false readings, and even in damage to or failure of the sampler. By way of example, such condensation can all too easily occur in consequence of conveying a portable gas monitor from an air-conditioned car to a humid out-of-doors environment.

The second type of sampling device is the "fixed" gas monitor; secured in place on site it continuously monitors levels of gaseous analytes at the chosen location, and triggers an alarm on a certain threshold analyte concentration being exceeded. Again, even with such a fixed monitor condensation can occur within or on the sensor, often as a result of temperature differences between the sampled gas and monitor, particularly where the gas is drawn from some different environment—for example, from an out-of-doors location to a room containing the monitoring equipment. And again, any formed mist may condense within the device, and on or within the sensor itself, resulting in false readings, and possibly damage to or failure of the monitor.

The invention is concerned with modifications to the device's internal structure intended to cope with the possibility of false readings caused by condensation and the like.

Gas detectors of the aforesaid ion-detection type usually have a walled (enclosed) sampling chamber within which the gaseous analytes are converted into ions (positively or negatively electrically-charged particles), forming a plasma. An electric field is applied across the chamber's cavity by means of two or more electrodes—a counter electrode at one voltage and a sensing electrode at a different, (usually effectively opposite) voltage—which are often a part of, or are contained within, the chamber walls. The ions are attracted through the gas to the appropriate electrodes, causing a signal current to flow, and this current is picked up, amplified, and displayed. Unfortunately, any contamination, such as condensation, on the surrounds of the chamber or the electrode supports and extending between the electrodes will provide an alternative route for electric current to flow between the electrodes, and if this happens then an increased but spurious signal is obtained from them which can obscure the small ion-derived current signal.

Although of course the problem of condensation can be tackled by using filters and water-absorbent materials in an attempt to remove any water vapour from the sampled air, this is often simply not practicable. Moreover, in some environments the capacity of the available filters and drying agents can readily be exceeded by the cumulative condensation of water from an admitted sample gas stream. In addition, such filters and agents frequently remove the sought-after analytes themselves from the gas sample before they ever reach the gas sample chamber.

Accordingly, a need exists to overcome the problems of mist and condensation with prior art ionization devices

SUMMARY OF THE INVENTION

The present invention therefore tackles the problem in a quite different way. Instead of attempting to prevent moisture reaching the sensor's ionisation chamber it seeks to prevent the inevitable spurious wall- or support-carried electrode current from being confused with the real, ion-derived current. And to achieve this result, the present invention provides an additional electrode at or nearly at the potential of the sensing electrode, which acts as a fence to "block" any current tracking along the walls or electrode supports. Typically this third (fence) electrode is placed within the ionisation chamber and physically located in or on the surrounds thereof between the counter electrode and the sensing electrode. This fence electrode does not affect— and is not affected by—the degree of condensation which may occur within the chamber, but provides a dramatically-extended integrity of measurement of gaseous ionisation under conditions of condensation or deposition of other electrolytically-conductive films within the chamber or on the electrode supports.

U.S. Pat. No. 5,479,022 dated 26 Dec. 1995, assigned to Varian Associates, Inc., describes an electron capture detector cell having a third (guard) electrode positioned between the cell field electrodes.

U.S. Pat. No. 4,454,425 dated 12 Jun. 1984, Robert A. Young, refers to a guard electrode in a particular configuration of photoioniser.

According to one aspect of the present invention there is provided an ionisation detector including at least one pair of counter and sensing electrodes at different electrical potentials measuring a plasma current between the electrodes in response to the presence of a gaseous analyte, wherein a third electrode is located between the counter and sensing electrodes and is maintained at an electrical potential substantially equal to that of the sensing electrode.

In one aspect, therefore, this invention provides an improved gas detector of the ion-detection type and having an enclosed sampling/ionisation chamber within which in use the gaseous analytes are converted into ions, an electric field being applied across the chamber by means of a counter electrode and a sensing electrode which are a part of, or are contained within, the chamber surrounds, in which detector there is, within the ionisation chamber and physically located in or on the surrounds thereof between the counter electrode and the sensing electrode, an additional electrode, which in use is maintained at or nearly at the potential of the sensing electrode and so which acts as a fence to "block" any current tracking along the surrounds.

More specifically, the invention provides an ionisation detector for the detection of a gaseous or vaporised material by its ionisation within an enclosed sampling chamber having:

inlet and outlet ports through which the material to be detected can be passed into and out of the chamber;

a sensing electrode positioned so as to pick up ionised material in the sampling chamber, from which a current is measured;

one or more other electrodes at a substantially different potential from the sensing electrode, at least one of which is positioned to pick up ionised material in the sampling chamber, and an additional fence electrode, incorporated within the surrounds of the chamber, positioned so as to pick up any net movement of electric charge along the surface of the sampling chamber's electrically-insulating wall (surround) members separating the sensing electrode and any other electrodes, but positioned so as not to pick up charged particles within the gaseous volume of the chamber, which fence electrode is at an approximately equal electrode potential bias to the sensing electrode, and from which the current may be measured.

The detector of the invention has a sampling chamber with inlet and outlet ports, a means of ionising gas admitted to the sampling chamber, and positive and negative electrode pair counter and sensing electrodes. Other than the position and status of the fence electrode and its relation to other gas sampling chamber members, the detector as so far defined is more or less a conventional ionisation detector, such as a photoionisation detector or flame ionisation detector, and needs no further comment. Nevertheless there are now provided brief descriptions of these two main types of detector.

In a photoionisation detector the sample gas is admitted to a walled sampling chamber which includes a source of light particles (photons) of sufficiently high energy to fragment gaseous analytes into ions, which ions are then separated and collected by electrodes forming part of the sampling chamber. The field applied between the electrodes is of the order of 100 V per millimetre. Analytes detected by the photoionisation detector include many volatile organic compounds (VOCs), to the part per billion level for particularly readily-ionised compounds such as isobutylene.

A flame ionisation detector depends upon exactly the same principle of measurement as the photoionisation detector. However, the source of ionisation of analytes is a small flame of hydrogen burning in the chamber. The detector is able to detect almost all VOCs to the part per billion level by volume, and although the detector operates at temperatures where condensation is unlikely to occur within the sample chamber, water is a product of hydrogen burning, and this water can itself cause condensation, particularly when the flame is extinguished.

An important feature of the detector of the invention is the position of the fence electrode in relation to the other electrodes and any other sampling-chamber surround members. This is now discussed further.

Hereinafter, for convenience, the following conventions will be used. The net positive or negative movement of electric charge in the gaseous volume defined by the sample chamber is referred to as "plasma current", and the corresponding movement of charge along deposits on the sampling chamber insulating surround members is described as "electrolytic current". The invention refers to at least one electrode other than the sensing electrode positioned so as to pick up ionised material; this one (or more) such electrode is a "counter electrode". Finally, for reasons of clarity, it is advantageous to refer all potentials to a common reference potential, referred to as a "ground potential".

The sensing electrode converts the plasma current into an electric current. The current is then drawn, amplified and measured. By way of example, the sensing electrode potential is conveniently electronically configured to be within a few millivolts of the detector's ground potential. The fence electrode is also maintained at a potential close to the detector's ground potential. The counter electrode is caused to be at a potential very much more negative or positive than the potential of the sensing or fence electrodes, depending on the means of ionisation.

In the absence of the fence electrode, the sampling chamber surrounds provide a route for electrolytic current to pass between the counter and sensing electrodes, even if the surrounds are made of electrically-insulating material. Specifically, a film of electrolytically-conducting material, such as water or water-containing contaminants, may deposit on the chamber walls, providing a contiguous conducting path between the electrodes. The fence electrode provided by the invention is placed as a wall member, which ensures that there are no or very few contiguous paths that can be traced between the sensing and counter electrodes which do not cross over that fence member. Because the electric potential of the fence electrode is caused to be very close to that of the sensing electrode it takes up almost all of the electrolytic current, and any residual electrolytic current conveyed between the fence and sensing electrodes is effectively negligible as compared with the small plasma current induced between the counter electrode and sensing electrode.

The fence electrode provided by the invention is positioned within the gas sampling chamber so that it makes substantial physical contact with any electrolytically-conductive surface films on the sampling chamber's insulating wall members or the electrode supports. By way of preferred example, the fence electrode is either nearly flush with chamber walls or slightly recessed (so it is rather like a "Ha-Ha"!), so as to be caused to contact condensation depositing on chamber walls without affecting the movement of plasma current between the counter and sensing electrodes. Serendipitously, the purpose of the counter and sensing electrodes is to induce plasma flow, and therefore these electrodes are commonly directed in ionisation chambers to apply a field across the sample chamber cavity, whereas a fence to prevent electrolytic flow between the electrodes is neatly disposed at or near the sample chamber walls without unduly affecting either the plasma electric field or the collection of plasma current therefrom. A fence electrode of approximately 0.2 mm in thickness and recessed by approximately 0.1 mm is well suited to this purpose, for gas sampling chambers of approximately 1 cm dimensions.

The shortest electrolytic path between the fence electrode and the sensing or counter electrodes is not of critical importance to the effectiveness of the fence electrode provided by the invention. However, in many ionisation detectors the shortest electrolytic path between counter and sensing electrodes is small. In such detectors, and by way of example only, for ease of fabrication it is commonly convenient to place the fence electrode mid-way between the two electrodes. To prevent significant electrolytic current being registered by the sensing electrode due to a few millivolts of potential difference between it and the fence electrode the shortest path between them is preferably more than 0.5 mm.

The electrolytic current collected by the fence electrode can be amplified and measured in much the same way as the plasma current at the sensing electrode. Ionisation detectors provided by this invention can thus be used to provide an important diagnostic regarding the cleanliness of the gas sampling chamber. Over time, and particularly when exposed to highly polar organic volatiles such as methylene chloride, deposits of hygroscopic material tend to accumulate on detector walls or electrode supports. These deposits aggressively adsorb water from the sample gas even if its relative humidity is less than 100%. Such instances will be evident from continuous or frequent incidents of high fence current, and can be used to flag a message or alarm indicating that the detector may require cleaning or replacing.

As can now be understood, improved detectors of the invention provide a means to measure the severity or persistence of condensation within the sample chamber, indicating whether actions such as sample-gas-drying or detector-servicing need be undertaken if condensation or electrolytically-conductive film deposition is particularly severe or persistent. In this way the improved detectors provide extended measurement integrity, and are thus of particular value in applications frequently relating to health and safety, where such integrity is an essential pre-requisite to deployment of these detectors.

It is important to note that the use of a fence electrode—is applicable to all detectors engaging electrodes across a high-impedance ion conducting medium (such as ion-conducting ceramic), where some alternative pathway due to contaminants including condensation can compromise the ion current signal measurement.

A further aspect of this invention concerns photoionisation detectors, and relates in particular to such detectors that enable gases, particularly air, to be sampled for constituents which form ions when exposed to light of sufficient energy. These gases are known as photoionisable gases, and of much interest are photoionisable gases that are harmful or dangerous to health, that may present a fire risk, or that indicate the failure of equipment designed to contain them in gaseous or liquid form.

Photoionisation detectors usually incorporate a chamber through which sample gas is caused to pass by means of suitable tubing, pumps and fans. The chamber is exposed to light particles, known as photons; a proportion of the photons have sufficient energy to break any photoionisable gas molecules within the sample into electrically charged molecular fragments, known as ions. This process is known as photoionisation and the chamber itself is described as a photoionisation chamber. Each photoionisation event engages one photon, and causes equal numbers of positive and negatively-charged ions to form, usually one of each. An electric field is applied across the chamber's cavity by means of two or more electrodes which are a part of, or are contained within, the chamber walls. The ions are attracted to the electrodes causing a current to flow, which current is amplified and displayed, and can be read to provide an indication of the presence of the sought gas molecules.

A presently favourable arrangement of components within a photoionisation chamber by which high performance of the device is assured uses UV light. Outside heavily industrialised areas and away from congested traffic, air out-of-doors typically contains less than a few parts per million by volume (ppm) of gases photoionisable by photons of energy between 8 and 12 electron volts (eV), whereas there are many gases—including most volatile organic carbon compounds—which are photoionisable by photons of this energy. Light of photon energies in this range can be generated from readily—commercially—available UV discharge electrodeless lamps of a few centimeters length, and about one centimeter diameter. The lamps contain an inert gas such as krypton or xenon, or deuterium or mercury vapour, at a few millibars of pressure. Borosilicate glass is a suitable material for the body of the lamps, terminating at one end with a wall member comprising a flat round disc of magnesium fluoride and calcium fluoride, which are transparent to photons in the energy range of interest.

It is convenient to remove—and so detect—the formed ions by means of electrodes located no more than a millimeter from the lamp face. The reason is that light in the range 8 to 12 eV is adsorbed not only by photoionisable gases but also by other gaseous constituents of air, such as humidity, and an electrode network extending more than about one millimeter from the lamp face too easily gives rise to a response to a sample gas which varies with its humidity. This is undesirable.

Furthermore, positive and negative ions are electrically attracted to each other, and, at concentrations of a few ppm of readily-ionisable gas in air subjected to typical lamp light, over short times—even as short as a few hundredths of a second—recombine in appreciable numbers to form electrically neutral molecules, which are not attracted by the electrodes and hence do not contribute as they ought to a photoionisation current (plasma current). At any particular light intensity, ion recombination increases approximately as the square of ionisable gas concentration in the sampled air, because the probability of ion recombination is proportional to the concentrations of both positive and negative ions, and the ions are formed in almost equal numbers approximately in proportion to the concentration of ionisable gas.

Thus, it is found that to obtain a photoionisation current due to a photoionisable gas which is proportional to its concentration, enabling reliable measurements to appreciably high concentrations of ionisable gas, say 1000 ppm, the presently favoured photoionisation detectors commonly embody two electrodes whose metalwork disposed within the ionisation chamber is located within a millimeter of the lamp window. The electrodes are of planar form, and of thickness less than a few tenths of a millimeter. One electrode, known as the anode, is caused to be at a positive electric potential relative to the other (the cathode), and abuts or is otherwise located very close to the lamp window, attracting negatively-charged ions. The anode contains a means of admitting light through it, for example by containing slots or holes. The second electrode, known as the cathode, is caused to be at a negative potential relative to the first (the anode), and is placed parallel to and within a millimeter of the anode; it attracts positively-charged ions. This arrangement assures that positive ions, which form more contaminating products than negative ions, are conveyed away from the lamp window. In terms of the nomenclature used previously, the cathode functions as a counter electrode.

A problem presented by an electrode arrangement of this sort is that any cathode metalwork exposed to UV photons of energy exceeding a few electron volts ejects electrons which are attracted to the anode and thereby cause a current to be registered irrespective of the presence or otherwise of any photoionisable gas within the photoionisation chamber. Hereinafter, for convenience this current will be referred to as a "photoelectron current". By way of example, the photoelectron current in a detector incorporating a krypton lamp and a cathode comprising uniform metalwork can exceed the photoionisation current caused by 50 ppm of a readily-ionisable gas such as isobutylene. Since the photoelectron current varies unpredictably with cleanliness or age of the lamp—according to the intensity of light issued therefrom—the attenuation or elimination of this affect is highly desirable. The cathode metalwork exposed to light can be reduced to some extent by the presence of slots or holes, but, should cathode metalwork disposed within the photoionisation chamber be too scarce, linearity of photoionisation current with concentration of photoionisable gas is adversely affected. Alternatively, material opaque to those photons having sufficient energy to eject electrons from the cathode metalwork can be disposed between the cathode and lamp window. However, this arrangement is also found to affect linearity of photoionisation current with photoionisable gas concentration because of there being limited cathode metalwork readily accessible to positive ions.

The present invention provides a means of substantially preventing photoelectrons generated at a cathode within a photoionisation chamber from migrating to an anode proximal to a UV lamp window which forms one wall of the photoionisation chamber, and achieves this without unduly restraining ions from movement between the two electrodes, or significantly preventing light from access to the cathode. Moreover, as described above the present invention provides a means of registering the presence of condensation within a photoionisation chamber, whilst enabling moderate condensation to occur without loss in integrity of measurement of a photoionisation current.

According to this aspect of the present invention there is provided a photoionisation detector including at least one pair of counter and sensing electrodes at different electrical potentials measuring a plasma current between the electrodes in response to the presence of a gaseous analyte, wherein a third electrode located between the counter and sensing electrodes and maintained at an electrical potential substantially equal to that of the sensing electrode collects photo-induced current derived from the counter electrode.

In this aspect, therefore, the invention provides a photoionisation detector for the detection of a gaseous or vaporised material by its ionisation within an enclosed sampling chamber having:

inlet and outlet ports through which the gaseous material to be detected can be passed into and out of the chamber, an anode positioned so as to pick up negatively-ionised material in the sampling chamber, and a cathode, at a substantially different potential from the anode electrode, which is positioned to pick up positively-ionised material in the sampling chamber;

wherein the chamber also has an additional fence electrode, positioned substantially between the first two electrodes, and of an electrode potential bias approximately equal to that of the anode, so as both to pick up any net movement of electric charge along the surface of the sampling chamber's electrically-insulating surround members separating the anode and cathode, and also to pick up electrons ejected from the cathode in consequence of its exposure to UV light, and wherein there is means to measure the electric current from one or more of the electrodes.

The detector of the invention has a sampling chamber with inlet and outlet ports, a means of ionising gas admitted to the sampling chamber, and a positive and negative electrode pair (the anode and cathode). The detector may also include a means of conveyance of sample gas to and from the gas sample chamber, and a source of UV photons, usually a UV lamp, located in close proximity to the detector anode. However, other than the position and status of the fence electrode and its relation to other gas sampling chamber members, the detector as so far defined is more or less a conventional photoionisation detector, and needs no further comment.

The detector of the invention is now described by reference to the position of the fence electrode in relation to other electrodes and other sampling chamber sampling members.

Hereinafter, the net positive or negative movement of electric charge in the gaseous volume defined by the sample chamber, which plasma current is caused by the photoionisation of gaseous or volatile material within the sample chamber, is for convenience referred to as "photoionisation current"; as previously the corresponding movement of charge along deposits on the sampling chamber insulating surround members is for convenience described as "electrolytic current"; and the photo-induced current caused by the photoejection of electrons from the cathode is for convenience called the "photoelectron current". As previously, it is advantageous to refer all potentials to a common reference potential, hereinafter for convenience referred to as a "ground potential".

The relative electric potentials and functionality of electrodes in accordance with the invention are now described.

A sensing electrode whose current is to be amplified and measured is conveniently electronically configured to have a potential within a few millivolts of the detector's ground potential. Since the fence electrode is maintained at a potential close to that of the anode, and since its current can be measured according to the invention, it is usually convenient to cause both the anode and fence electrode to be at the detector's ground potential. The cathode is then caused to be at a potential very much more negative than the potential of these two electrodes, typically 200 V more negative, for each millimeter of spacing between the cathode metalwork and other electrode metalwork.

As discussed previously, in the absence of the fence electrode the sampling chamber surrounds provide a route for electrolytic current to pass between the anode and cathode, even if the surrounds are made of electrically-insulating material. Specifically, a film of electrolytically-conducting material, such as water or water-containing contaminants, may deposit on the chamber walls, providing a contiguous conducting path between the electrodes. The fence electrode provided by the invention extends and projects from the walls of the chamber between the cathode and anode, so that are no or very few contiguous paths that can be traced between the anode and cathode which do not cross over that fence. Because the electric potential of the fence electrode is caused to be very close to that of the anode, almost all the electrolytic current is conveyed away via the fence electrode, and the electrolytic current conveyed between the fence electrode and anode is negligible as compared with the small plasma current induced between the cathode and anode.

The fence electrode provided by the invention has metal surfaces able to pick ions from the sampling chamber, and most particularly electrons ejected from the cathode as a result of light incident thereon. The fence electrode allows light to impact on the cathode because it—the fence electrode—is perforated. Ideally the cathode and preferably all three electrodes are perforated. Typically the fence electrode and preferably all three electrodes comprise thin slats or wires, or an open honeycomb structure, which allow almost all the light—and the gas—to pass through. The slats or wires of the fence electrode are located within close proximity of the cathode metal work to collect almost all the photoelectrons generated therefrom, without significantly preventing ions generated elsewhere within the sample chamber from being attracted to the anode or cathode according to their charge. Electrode surfaces within the sampling chamber are disposed such that distances of closest approach between the anode and cathode are greater than distances of closest approach between the fence electrode and the cathode metalwork, or between the fence electrode and anode metalwork.

All three electrodes are preferably substantially planar, typically made from metal sheeting, and are arranged substantially parallel to each other, with the fence electrode being placed between the anode and cathode. A fence electrode made from sheet of approximately 0.15 mm in thickness and positioned between 0.2 mm to 1 mm from the plane of a parallel anode and cathode made from similar sheeting is well suited to this purpose, for gas sampling chambers of approximately 1 cm diameter. This arrangement of electrodes will hereinafter for convenience be described as an "electrode stack". Sampling chamber walls enabling reliable separation of electrodes in the electrode stack are conveniently comprised of sheets of UV light resistant material such as PTFE.

Each of the electrodes within an electrode stack may advantageously contain parallel slats of metalwork, with corresponding parallel slots. It is then preferable for each of the slats and slots of different electrodes to be substantially mutually parallel as well, and for slats of different electrodes to be substantially equally spaced, such that when the electrode stack is viewed from various oblique angles the slats of different electrodes appear superposed. By this means the anode slats are most optimally and effectively electrically screened from the photoelectrons generated at the cathode. When viewed normal to the plane of an electrode stack, it is preferable for slots in the cathode to superpose the slots in the fence electrode and preferably also in the anode.

Each of the electrodes within an electrode stack may alternatively contain a lattice of metalwork, with corresponding holes. It is then preferable for the holes of different electrodes to be disposed such that when the electrode stack is viewed from various oblique angles the holes of different electrodes appear superposed.

The slats or other lattice of metalwork forming the anode and fence electrode are preferably as thin as can be reasonably fabricated—typically 0.15 to 0.3 mm in width, with corresponding slots or holes 0.5 to 1 mm in width. Any slots or holes in the cathode provided by the present invention may also contain means of gas movement through it, as described above. However, the total area of cathode metalwork disposed within the sample chamber and hence exposed to incident light, hereinafter referred to as the "effective area", is substantially greater than that of the anode or fence electrode. By this means the linearity of response of the photoionisation chamber to increasing concentrations of a photoionisable gas is found to be extended.

The electrolytic and photoelectron current collected by the fence electrode can be amplified and measured in much the same way as the current at the anode. As discussed above photoionisation detectors provided by this invention can thus be used to provide an important diagnostic regarding the cleanliness of the gas sampling chamber.

Additionally, by comparing the current collected by the fence electrode with and without a photoelectron component, for example by subtracting one from the other, it is possible to discriminate between the electrolytic and photoelectron currents. These two aspects can be used as a measure of the degree of contamination or condensation within the chamber and of lamp efficiency, respectively. This aspect of the invention provides a method of operating a photoionisation detector as described above wherein: (a) collection of the photo-induced current derived from the cathode is intermittently disabled; (b) the current collected during such period of disablement is compared with the current collected by the third (fence) electrode when not so disabled; and (c) such comparison is used as a measure of light source efficiency.

Preferably, collection of the photo-induced current is disabled by intermittent shutting-off of the light source. Alternatively, collection of the photo-induced current may be disabled by intermittently maintaining the electrical potential of the third (fence) electrode substantially equal to that of the cathode, for example by switching the voltage applied to the fence electrode from one value to the other.

BRIEF DESCRIPTION OF THE DRAWINGS

Embodiments of the invention are now described, though by way of illustration only, with reference to the accompanying diagrammatic Drawings in which.

DETAILED DESCRIPTION OF THE INVENTION

It should be understood that these embodiments are only examples of the many advantageous uses of the innovative teachings herein. In general, statements made in the specification of the present application do not necessarily limit any of the various claimed inventions. Moreover, some statements may apply to some inventive features but not to others. In general, unless otherwise indicated, singular elements may be in the plural and vice versa with no loss of generality.

Figure 1:
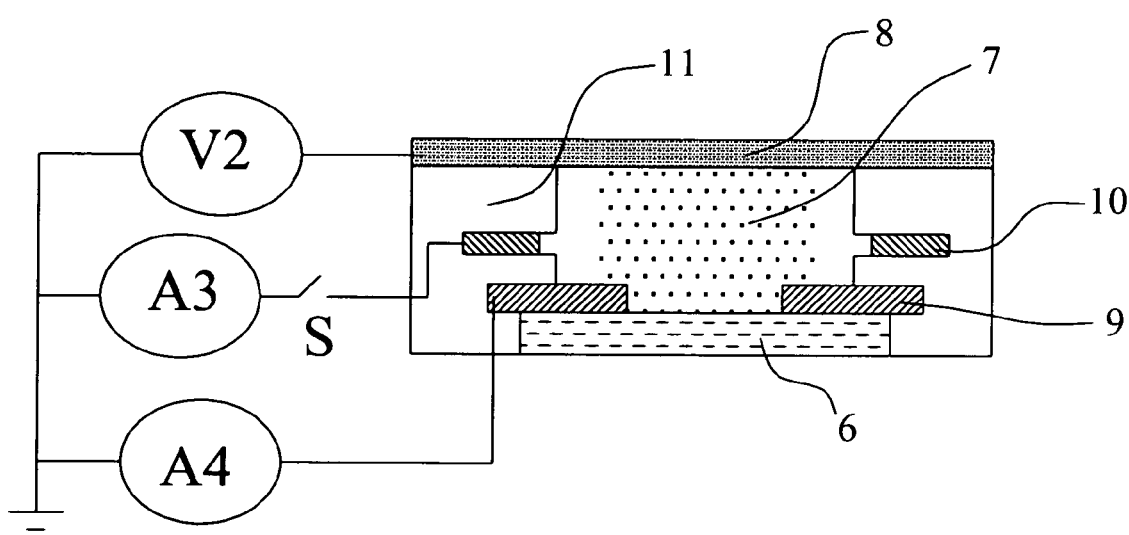
FIG. 1 shows a schematic representation of a photoionisation detector including a fence electrode according to the invention.

In FIG. 1 a photoionisation detector gas sampling chamber is depicted, where high energy light (from a source not shown) is caused to pass through a window of transmitting material (6). Ions are generated in the sample chamber gaseous space (approximately depicted by the area (7)). Positively-charged ions are picked up by the counter electrode (8) whilst negative ions are picked up by the sensing electrode (9). Between these electrodes is located the fence electrode (10), supported by electrically insulating material (11).

The window (6) is commonly made of magnesium fluoride, which transmits ultraviolet light (of photon energy to 10.6 eV) from a lamp (not shown). Window (6) comprises an integral enclosing member of the lamp. Electrodes (8), (9) and (10) are again conveniently made of an electrically-conductive corrosion-resistant material such as stainless steel. The insulating walls preferably comprise PTFE.

Plasma generated in the vicinity of the gaseous space (7) is caused to migrate to electrodes (8) and (9) by virtue of the negative field generated at the counter electrode (8) relative to ground. The distance between the counter electrode (8) and the window face (6), partially defining wall chamber members, is optimally 1–2 mm, and the voltage applied (by source V2) is of the order of 200 V. The fence electrode (10) is preferably set back or recessed within the PTFE walls so that the pathways available to ions to access the electrode are restricted, but the fence electrode is not so recessed into the PTFE as to afford the possibility of condensation bridging the recess and provide thereby an electrolytic path between the electrodes (8) and (9) and no such path between (8) and (10).

In FIG. 1, the amplifier circuitry (A3, A4) enables electrolytic and plasma current measurements from electrodes (10) and (9) respectively. In this particular embodiment a switch (S) is included which enables the effect of the fence electrode to be measured as presented in FIGS. 2 and 3.

Figure 2:
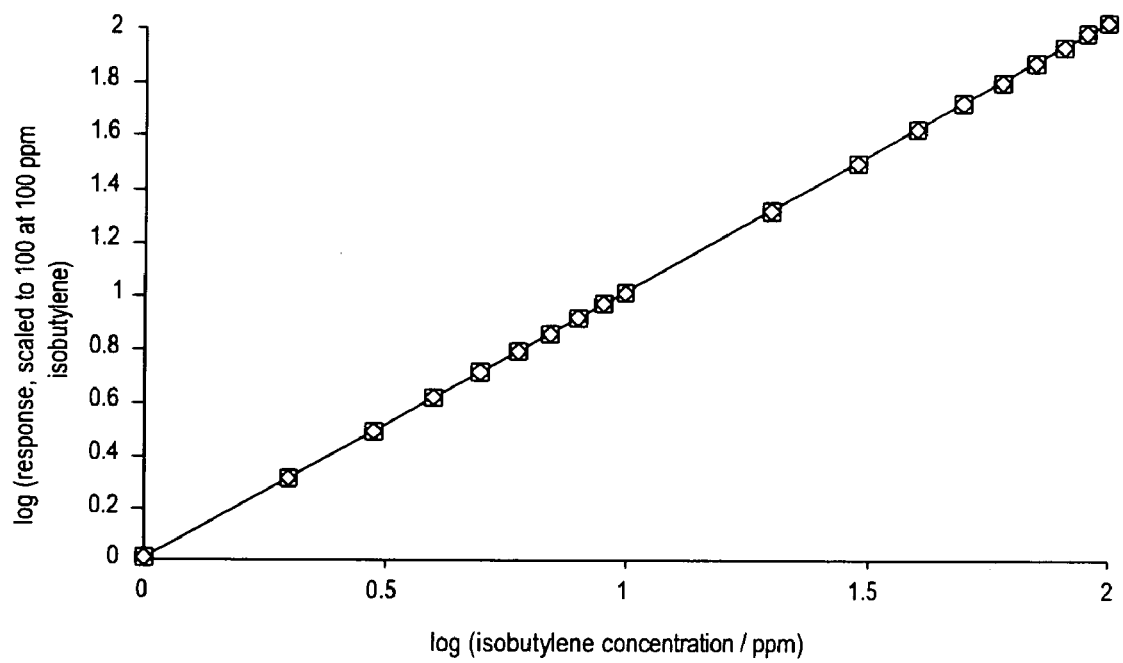
FIG. 2 shows graphically the relative output of the improved photoionisation detector of FIG. 1 in response to varying concentrations of isobutylene gas in air at relative humidity of 60%, with and without the removal of any current by the fence electrode.

FIG. 2 shows the output from a photoionisation chamber's amplified current from the sensing electrode, such as is depicted in FIG. 1 (A4), against known concentrations of isobutylene gas injected stepwise into a large drum previously filled with air from a clean outside location at relative humidity 60%. The drum volume (of some 91.25 litres) was sufficiently large for the continuous removal of the gas into the photoionisation detector not to significantly effect the concentration of isobutylene within the drum.

The response of the amplifier circuitry (A4 in FIG. 1) is shown. Measurements carried out are depicted as square datum points with the switch S closed and the fence operative, and as diamond datum points with the switch S open and the fence inoperative. As can be seen, the relative responses are the same irrespective of the switch being closed or open, illustrative of no electrolytic current being drawn by the fence when actively drawing current. It can be concluded that the fence does not deleteriously affect the performance of the photoionisation detector.

Figure 3:
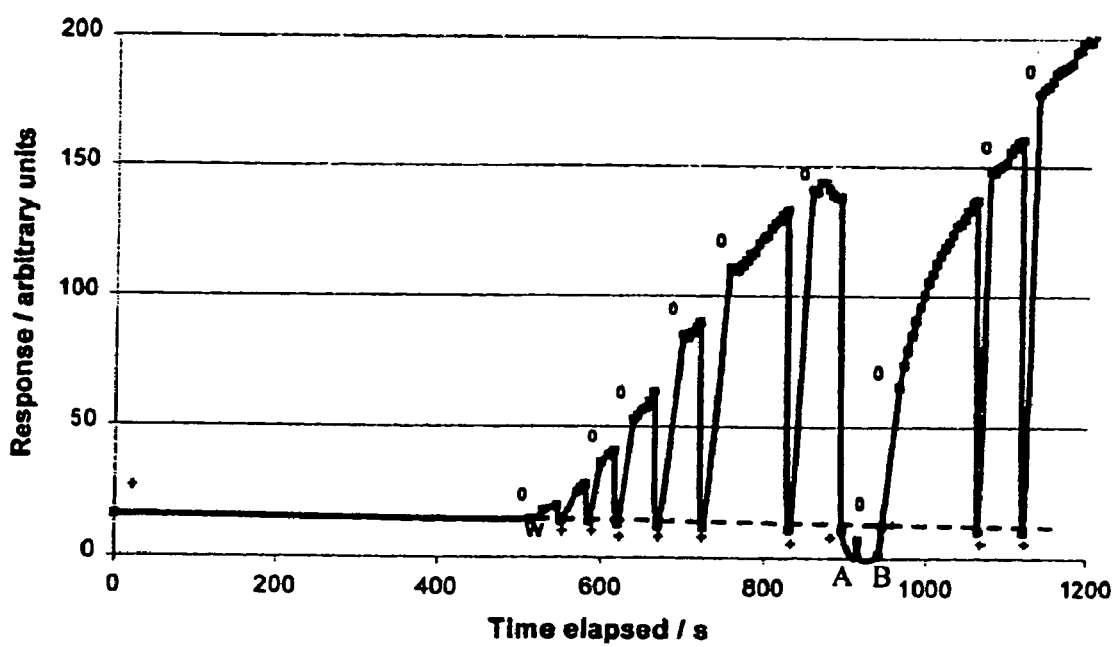
FIG. 3 shows the continuous output of the photoionisation detector of FIG. 1 in response to an invariant concentration of 1000 ppm methylene chloride, with and without the removal of any current by the fence electrode.

In FIG. 3 a sequence of events is recorded from the detector depicted in FIG. 1 (using amplifier circuitry A4). Using the same equipment as utilised to produce the FIG. 2 figures, air of relative humidity 60% was initially admitted to the drum together with sufficient methylene chloride liquid to volatise within the drum so as to cause there to be present within the drum 1000 ppm methylene chloride.

The mixture of gases was caused to be continuously admitted to the photoionisation detector, and the amplified current drawn from the sensing electrode was continuously measured. The response over some 500 seconds of sequential monitored data is shown, and it can be seen that the signal did not change significantly irrespective of whether the switch S, FIG. 1, was open or closed.

In the absence of any subsequent changes to the gas concentration within the drum, the signal could be anticipated to continue along the dashed line. However, after about 500 seconds of measurement sufficient water was injected into the drum of agitated gas to cause its relative humidity to increase to 100%. At various times—indicated by 'O', FIG. 3—the switch S was opened, whilst at other times—indicated by '+'—the switch was closed. It can be seen that between 500 and about 850 seconds elapsed, the amplified current signal from the sensing electrode increased when the switch was open (and thus the fence was inoperative), but continued near the anticipated value for 60% humidity when the switch was closed and fence was thus operative. Hence, the effect of water deposition on the photoionisation detector's wall chambers is seen to be eliminated by the fence electrode provided by the invention.

Some decrease in response over anticipated values might be attributed to water condensation on the cell window (6) and perhaps also water vapour or mist within the cell volume chamber gaseous volume (7) reducing the photon flux within the volume (7), with consequent decrease in the plasma density within this volume. However, the decay in response is not severe, and can to some extent be compensated by measurement of the fence current provided by amplifier circuitry A3.

At time A the probe was detached from the drum containing the methylene chloride saturated with water, and was expose to well-ventilated clean air at 60% relative humidity. As can be seen, the response dropped to zero with the switch closed, but continued to indicate briefly a small amount of contamination with the switch open. After some 930 seconds, at point B, the probe was re-connected to the drum and the effect of condensation, and the fence electrode in preventing its registration by the sensing electrode, as provided by the invention, was again demonstrated.

Figure 4:
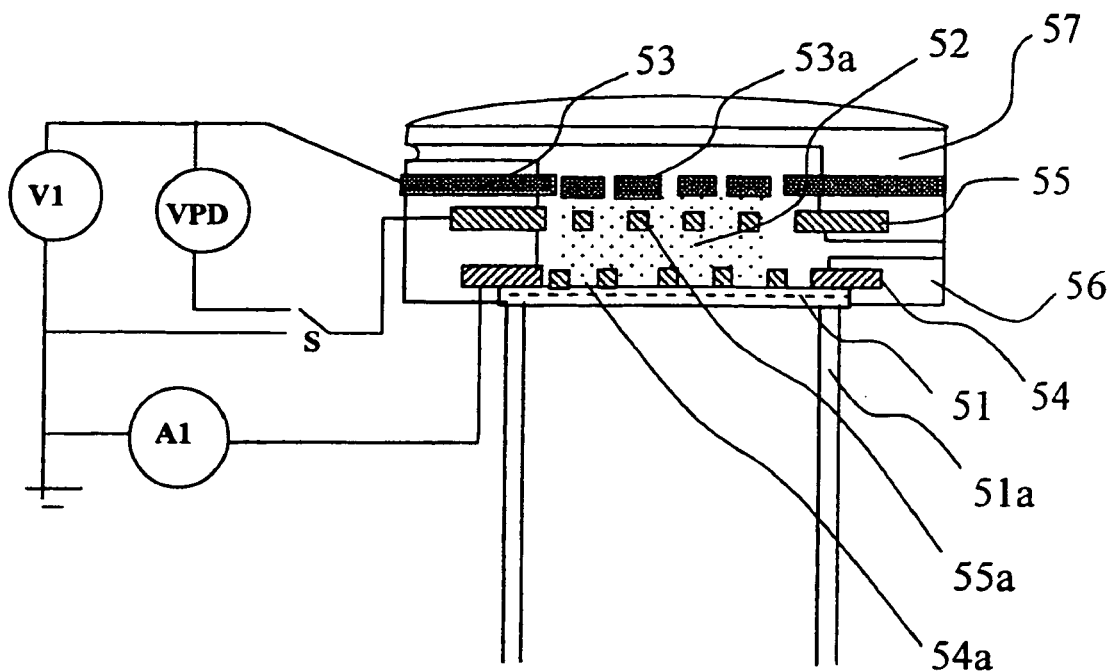
FIG. 4 shows a schematic representation of a second form of photoionisation detector including a fence electrode according to the invention which additionally collects the photoelectron current.

In FIG. 4 a second photoionisation detector gas sampling chamber is depicted. The detector included a conventional electrodeless lamp containing a rarefied atmosphere of krypton gas, illuminated by means of rings of 14 mm diameter (not shown) placed circumferentially about the cylindrical lamp body of the 12 mm diameter lamp, one ring being approximately 2 mm from the lamp window (51), and one ring being approximately 12 mm from the lamp window. The rings were subjected to a variable electric field causing the lamp to illuminate. High energy light was thereby caused to pass through a 12 mm diameter, 1 mm thick, disc of magnesium fluoride, depicted as (51) in FIG. 4, which forms part of a sampling chamber wall. Part of the cylindrical walls of the lamp (51a) is also depicted.

The chamber's other electrically-insulating material walls are (56) and (57). The insulating walls (56) and (57) preferably are composed of PTFE. The sampling chamber walls (56) and (57) also serve to support the electrodes (53), (54) and (55). In the embodiment of the invention shown, gas is admitted and dispelled from the sampling chamber by means of a cavity in insulating wall members (56) and (57) respectively. The members (57), (53), (55), (56) and (54) are clamped together so as to enable gas drawn by means of a pump (not shown) attached to gas exit means in (57) to draw gas into gas entry means in (56).

A potential of −190 V is applied by means of voltage source V1 to the cathode (53), relative to the anode (54). By use of the switch S, the fence electrode (55) is caused to be at either −190 V or 0 V relative to the anode (54). Ions are generated in the sample chamber gaseous space approximately depicted by the area (52). Positively-charged ions are picked up by the cathode (53) whilst negative ions are picked up by the anode (54). Fence electrode (55) provided by the invention is located between them.

Electrodes (53), (54) and (55) are conveniently made of an electrically conducting corrosion-resistant sheeting, such as 1.5 mm thick stainless steel sheet, etched so as to contain slats as shown in FIG. 4. Cathode slats (53a) are of approximately 0.5 mm in width, whilst other slats are 0.15 mm in width. PTFE members (56) and (57) ensure separation between electrodes (53) and (55) of 0.25 mm, and between electrodes (54) and (55) of 0.75 mm.

Positive ions generated in the vicinity of the gaseous space (52) are caused to migrate to cathode (53) by virtue of its negative potential relative to electrodes (54) and (55). The distance between the cathode (53) and the transmitting material (51) is optimally no more than 2 mm, and the voltage applied by source V1 is of the order of −200 V.

The fence electrode (55) includes slats (55a) located directly below corresponding slats (53a) in the cathode and the slots (54a) between slats in the anode (54). Cathode slats (53a) are substantially thicker than the other slats.

In FIG. 4, the amplifier circuitry A1 enables the current collected by the anode (54) to be measured. A variable potential divider VPD enabled the effect of the fence electrode (55) to be measured when caused to be at various applied potentials between that of the cathode (53) and that of the anode (54).

The performance of a device provided by the invention is now presented by way of example only, and to show how the invention has been used to improve the performance of a photoionisation detector.

Gas tubing is attached to the gas entry means at one end. The other end is attached to a 91 litre metal drum containing a fan to enable gas within the drum to be readily agitated. The drum has a lid that can be removed to enable its contents to be purged with air in a well ventilated room. With the drum lid sealed, isobutylene gas is admitted to the drum by means of inserting a syringe into a pin hole in the drum lid. Gas is injected stepwise, and the signal from amplifier A1 is measured following each stepwise injection of gas, at both positions of the switch S.

Figure 5:
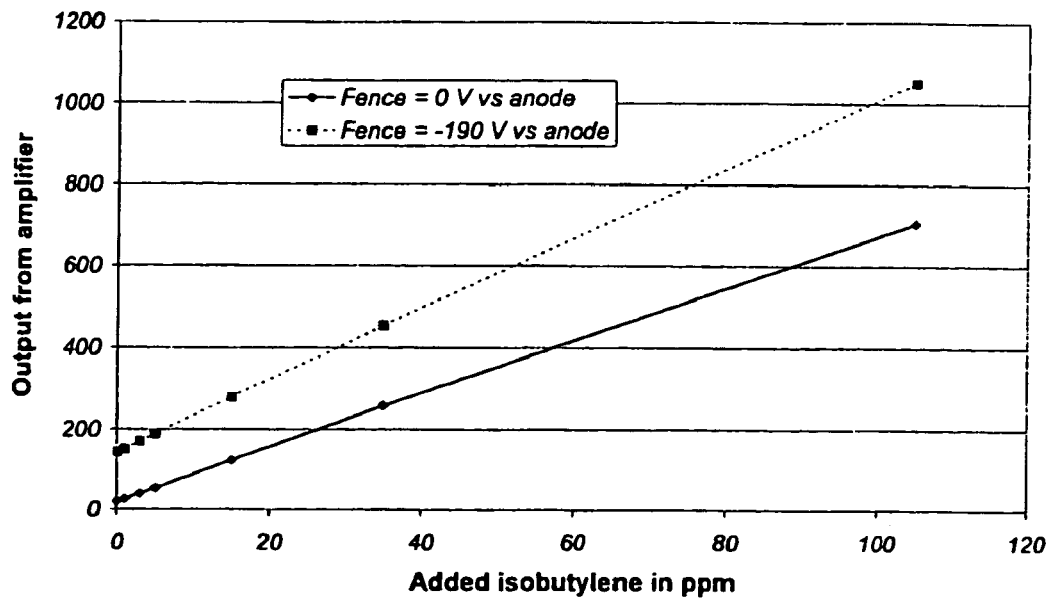
FIG. 5 shows graphically the relative output of the photoionisation detector of FIG. 4 in response to varying concentrations of isobutylene gas in air with and without incorporation of a fence electrode provided by the present invention.

In FIG. 5, the response of amplifier A1 in FIG. 4 is plotted in arbitrary units versus the concentration of isobutylene added, for both switch positions. It can be seen that when the switch S causes the fence electrode (55) to be at the same potential as the anode (54), the signal at zero added isobutylene is some ten times lower than when the voltage is caused to be at the same potential as the cathode (53) (−190 V vs the anode), whilst the response to isobutylene is only some 1.3 times lower. The much reduced background signal ensures much decreased 'background drift' in the detector provided by the present invention.

Although a specific embodiment of the present invention has been disclosed, it will be understood by those having skill in the art that changes can be made to this specific embodiment without departing from the spirit and scope of the present invention. The scope of the present invention is not to be restricted, therefore, to the specific embodiment, and it is intended that the appended claims cover any and all such applications, modifications, and embodiments within the scope of the present invention.

The invention claimed is:

1. An ionization detector comprising:
   at least one pair of electrodes including at least a counter electrode and a sensing electrode at different electrical potentials measuring a plasma current between the electrodes in response to the presence of a gaseous analyte; and
   a third electrode located between the counter and sensing electrodes and maintained at an electrical potential substantially equal to that of a sensing electrode of the at least one pair of counter and sensing electrodes, wherein the third electrode is distinct from the counter electrode and the sensing electrode.

2. The ionization detector of claim 1, wherein the electrodes are located within an ionization chamber and the third electrode is disposed in or on a chamber surrounds.

3. The ionization detector of claim 2, wherein the third electrode is positioned to collect movement of an electric charge along an interior surface of the chamber surround while minimizing a collection of plasma current within an enclosed volume of the chamber surrounds.

4. The ionization detector of claim 3, wherein the third electrode is flush with an interior surface of the chamber surrounds or is slightly recessed in the chamber surrounds.

5. The ionization detector of claim 4, wherein the ionization chamber has at least one dimension of approximately 1 cm;
   wherein a field applied between the counter and sensing electrodes is of the order of 100 V per millimeter; and
   wherein the third electrode is approximately 0.2 mm in thickness, recessed by approximately 0.1 mm within an interior surface of the ionization chamber and is positioned more than 0.5 mm from the sensing electrodes.

6. The ionization detector of claim 1, wherein a current collected by the third electrode is amplified and measured.

7. A photoionization detector comprising:
   at least one pair of electodes including at least a counter electrode and a sensing electrodes at different electrical potentials measuring a plasma current between the electrodes in response to the presence of a gaseous analyte; and a third electrode located between the at least one pair of counter and sensing electrodes and maintained at an electrical potential substantially equal to that of a sensing electrode of the at least one pair of counter and sensing electrodes and wherein the third electrode collects photo-induced current derived from a counter electrode of the at least one pair of counter and sensing electrodes, wherein the counter electrode is a cathode, and wherein the third electrode is distinct from the counter electrode and the sensing electrode.

8. The photoionization detector of claim 7, wherein one or more of the electrodes are substantially planar and comprise a stack arranged substantially parallel to each other.

9. The photoionization detector of claim 7, wherein at least the third electrode is perforated.

10. The photoionization detector of claim 9, wherein at least the third electrode is composed of at least one of slats, wires, open honeycomb and lattice.

11. The photoionization detector of claim 9, wherein at least the counter electrode is perforated.

12. The photoionization detector of claim 11, wherein perforations of the at least counter electrode are substantially mutually parallel.

13. The photoionization detector of claim 11, wherein perforations of the counter electrode and the third electrode are superposed.

14. The photoionization detector of claim 11, wherein the perforations comprise substantially equally spaced slots.

15. The photoionization detector of claim 11, wherein an effective area of the counter electrode exceeds an effective area of the third electrode.

16. The photoionization detector of claim 15, wherein the perforations in the third electrode comprise slots or holes approximately 0.5 to 1 mm in width between slats approximately 0.15 to 0.3 mm in width.

17. The photoionization detector of claim 7, wherein the counter electrode is spaced up to 2 mm from a light-emitting surface; and
wherein the electrical potential between the counter electrode and other electrodes is approximately 200 V per millimeter of spacing between metal work for the counter electrode and metal work for other electrodes.

18. The photoionization detector of claim 7, wherein current collected by the third electrode is amplified and measured.

19. A method of operating an ionization detector comprising:
enclosing with a chamber at least one pair of electrodes including at least a counter electrode and a sensing electrodes at different electrical potentials, wherein a plasma current is measured between the electrodes in response to the presence of a gaseous analyte; and
collecting movement of electric charge along an interior surface of the chamber by at least one third electrode located between the counter and sensing electrodes, wherein the third electrode is maintained at an electrical potential substantially equal to that of a sensing electrode of the at least one pair of electrodes, and wherein the third electrode is distinct from the counter electrode and the sensing electrode.

20. The method of claim 19, wherein the current collected by the third electrode is used as a measure of a degree of at least one of contamination and condensation within the chamber.

21. A method of operating a photoionization detector comprising:
measuring a plasma current between at least one pair of, and wherein the third electrode is distinct from the counter electrode and the sensing electrode at different electrical potentials, wherein a plasma current is measured between the electrodes in response to the presence of a gaseous analyte; and
disposing a third electrode between the counter and sensing electrodes, wherein the third electrode is maintained at an electrical potential substantially equal to that of a sensing electrode of the at least one pair of electrodes so as to collect photo-induced current derived from a counter electrode of the at least one pair of electrodes, wherein the third electrode is distinct from the counter electrode and the sensing electrode.

22. The method of operating a photo ionization detector of claim 21, further comprising:
placing a light source to emit light therefrom into at least a portion of a chamber so that:
collection of the photo-induced current is intermittently disabled; the current collected during such period of disablement is compared with the current collected by the third electrode during a period when the current is not disabled; and
such comparison is used as a measure of light source efficiency.

23. The method of operating a photoionization detector of claim 22, further comprising:
shutting-off intermittently of the light source so that the collection of the photo-induced current is disabled.

24. The method of operating a photoionization detector as claimed in claim 22, further comprising:
maintaining intermittently the electrical potential of the third electrode substantially equal to that of the counter electrode so that the collection of the photo-induced current is disabled.

* * * * *

UNITED STATES PATENT AND TRADEMARK OFFICE
CERTIFICATE OF CORRECTION

PATENT NO.         : 7,046,012 B2                              Page 1 of 1
APPLICATION NO. : 10/479759
DATED               : May 16, 2006
INVENTOR(S)        : William Francis Houlton Dean et al.

It is certified that error appears in the above-identified patent and that said Letters Patent is hereby corrected as shown below:

Column 16, line 12 please add the following after at least one pair of "electrodes including at least a counter electrode and a sensor electrode"

Column 16, lines 13-14, please delete the following "and wherein the third electrode is distinct from the counter electrode and the sensing electrode"

Signed and Sealed this

Sixteenth Day of November, 2010

David J. Kappos
*Director of the United States Patent and Trademark Office*